United States Patent [19]

Rudolph et al.

[11] Patent Number: 5,268,365
[45] Date of Patent: Dec. 7, 1993

[54] NUCLEOTIDES, NUCLEOSIDES, AND NUCLEOBASES IN IMMUNE FUNCTION RESTORATION ENHANCEMENT OR MAINTENANCE

[76] Inventors: Frederick B. Rudolph, 4414 Silverwood St.; Charles T. Van Buren, 3024 University Blvd., both of Houston, Tex. 77005

[21] Appl. No.: 767,302

[22] Filed: Sep. 27, 1991

Related U.S. Application Data

[63] Continuation of Ser. No. 499,937, Mar. 27, 1990, abandoned, which is a continuation-in-part of Ser. No. 443,775, Nov. 30, 1989, abandoned, which is a continuation of Ser. No. 166,866, Mar. 11, 1988, abandoned.

[51] Int. Cl.$^5$ .............................................. A61K 31/70
[52] U.S. Cl. ....................................... 514/44; 514/885
[58] Field of Search ................... 536/23, 24, 26, 27, 536/28, 29; 514/43, 44, 45, 46, 47, 48, 49, 50, 51

[56] References Cited

U.S. PATENT DOCUMENTS

| | | | |
|---|---|---|---|
| 2,215,233 | 11/1937 | Ruskin | 514/47 |
| 3,914,450 | 10/1975 | Robbins et al. | 426/533 |
| 4,758,553 | 7/1988 | Ogoshi | 514/47 |

FOREIGN PATENT DOCUMENTS

| | | | |
|---|---|---|---|
| 1162853 | 2/1984 | Canada | 514/47 |
| 0178267 | 10/1984 | European Pat. Off. | 514/47 |
| 0216133 | 4/1987 | European Pat. Off. | 514/45 |
| 38-005291 | 5/1963 | Japan . | |
| 56-008307 | 1/1981 | Japan . | |

OTHER PUBLICATIONS

Van Buren et al, Transplantation, vol. 36, No. 3, pp. 350–352 (1983).
Van Buren et al, Transplantation, vol. 40, No. 6, pp. 694–697 (1985).
KulKarni et al, Archives of Surgery, vol. 121, pp. 169–172 (1986).
KulKarni et al, J. of Parenteral and Enteral Nutrition, vol. 10, No. 2, pp. 169–171 (1986).
KulKarni et al, Exp. Hematology, vol. 12, pp. 694–699 (1984).
Van Buren et al, Transplantation Proceedings, vol. XV, No. 4, pp. 2967–2968 (1983).
Van Buren et al, Transplantation Proceedings, vol. XIX, No. 4, pp. 57–59 (1987).
Fanslow et al, J. of Parenteral and Enteral Nutrition, vol. 12, No. 1, pp. 49–52 (1988).

*Primary Examiner*—Johnnie R. Brown
*Assistant Examiner*—James O. Wilson

[57] ABSTRACT

The invention provides a method of stimulating the immune function with the aid of a nucleobase source, the use of nucleobase sources for immunostimulation and compositions comprising such nucleobase sources. The invention also provides the use of nuclobase source for the maintenance of the immune function in the presense of protein depletion or protein starvation.

9 Claims, 3 Drawing Sheets

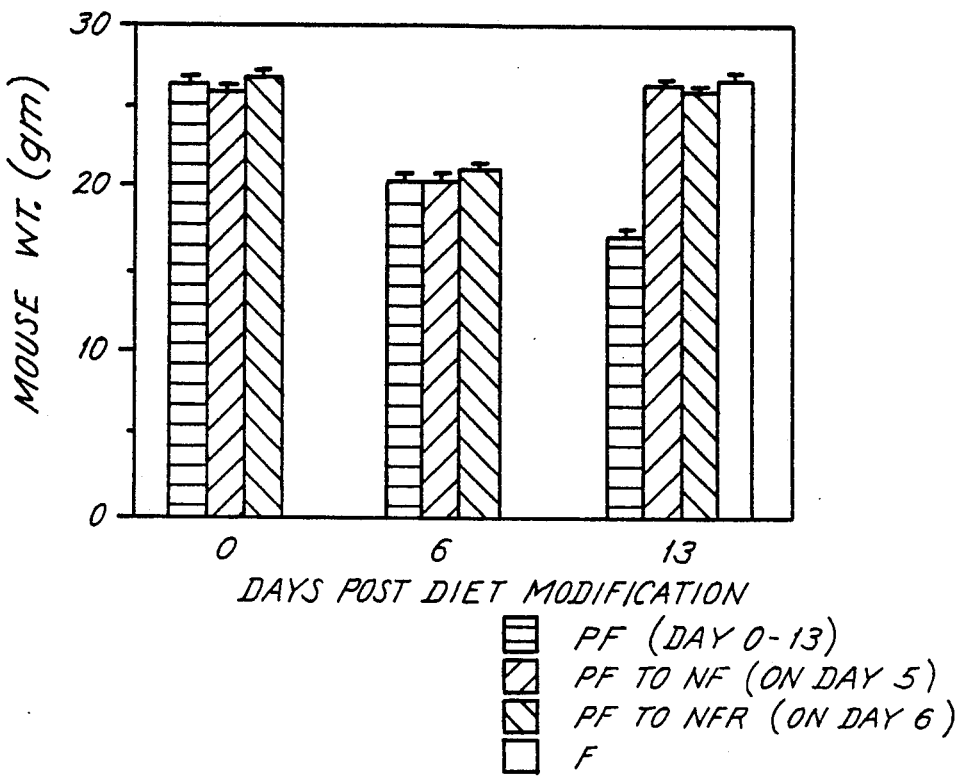
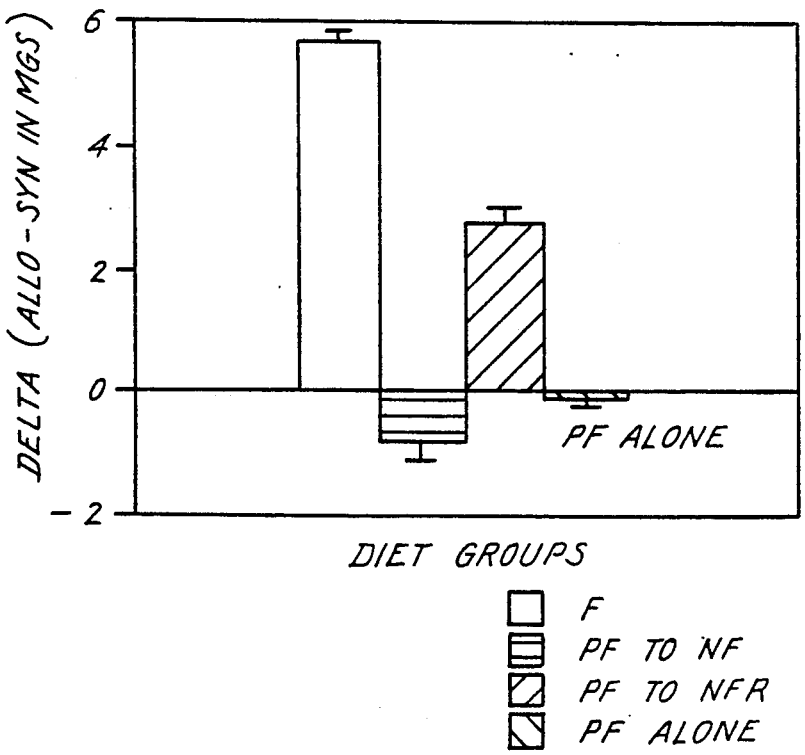

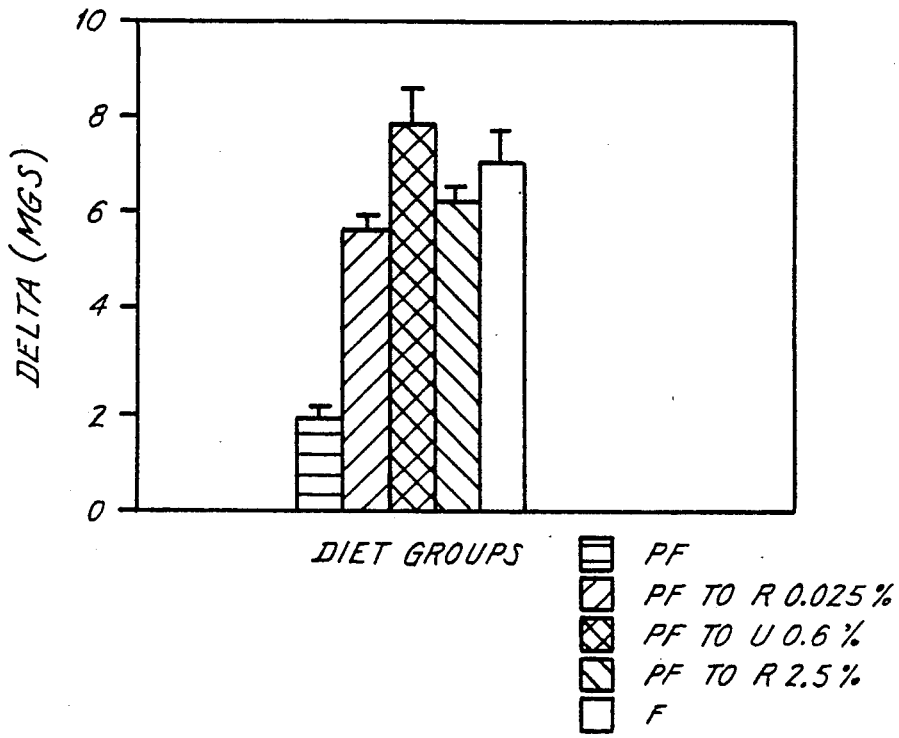
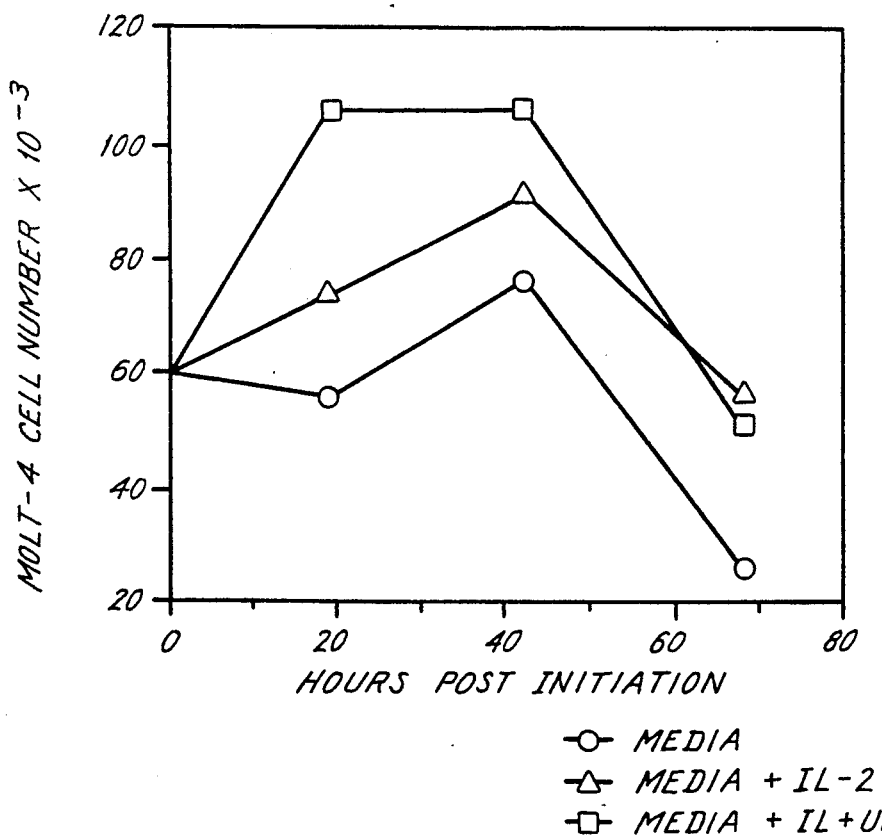

NUCLEOTIDES, NUCLEOSIDES, AND NUCLEOBASES IN IMMUNE FUNCTION RESTORATION ENHANCEMENT OR MAINTENANCE

This is a continuation of application Ser. No. 07/499,937, filed Mar. 27, 1990, which in turn is a continuation-in-part of application Ser. No. 07/443,775, filed Nov. 30, 1989, which in turn is a continuation of application Ser. No. 07/166,866, filed Mar. 11, 1988, all are now abandoned.

BACKGROUND OF THE INVENTION AND DESCRIPTION OF THE PREFERRED EMBODIMENTS

The invention relates to the influence of nucleobases on the immune function.

Purines and pyrimidines are synthesized in cells with amino acids as the principal precursors. It has now been found that a depressed immune response in mammals can be reversed by the addition of a nucleobase source to the formulation. In has also been found that the presence of nucleobases in the diet can prevent the immune suppression that occurs with protein or amino acid starvation. The prior art has maintained that the role of the nucleobases was to aid in utilization of protein or amino acids. As this invention demonstrates, this is clearly not true.

The stimulating effect of nucleobase sources on the immune system has been demonstrated by tests, e.g. in mice having depressed T lymphocyte function due to protein malnutrition. Further animal tests show that the depressed immune function of animals placed on a protein free diet cannot sufficiently be restored by protein repletion alone—even though this allows restoration of body weight—but requires the administration of a nucleobase source.

The invention provides a method of maintaining the immune function in the human and animal body even in the face of adverse nutrition including exclusion of amino acid or protein sources. Addition of the nucleobases allows maintenance of immune function under protein or amino acid starvation. The nucleobase source may be administered by any conventional route in solid or liquid form, in particular enterally, e.g. orally or nasally, or parenterally, e.g. in the form of injectable solutions or suspensions.

For use according to the invention the nucleobase source may be administered in conventional pharmaceutically or nutritionally acceptable formulation form. Examples of conventional pharmaceutically acceptable formulation forms include tablets, capsules and injectable forms which may contain the active agent in admixture with conventional pharmaceutically acceptable excipients, e.g. inert diluents or carriers, such as calcium carbonate, lactose and talc, granulating and disintegrating agents, e.g. starch and algenic acid, flavouring, colouring and sweetening agents, binding agents, e.g. starch or gelatin, lubricating agents, e.g. magnesium steratte and talc.

Examples of conventional nutritionally acceptable formulation forms include conventional diets, e.g. formula diets containing the nucleobase source in admixture with sources for essential amino acids and energy supply such as for proteins, carbohydrates and/or fat as desired.

Such dietary compositions may for example supply from 400 to 2000 Kcal, e.g. 1500 Kcal per day. The compositions of the inventions may be enriched with vitamins, such as vitamin C, minerals, such as iron, trace elements such as Selenium and optionally other elements, depending on the needs of the subject to be treated.

Formulations for enteral application are conveniently in solid or liquid form.

Nucleobase sources suitable for use in the method of the invention comprise, and more preferably consist essentially of natural nucleobases, nucleosides, nucleotides, RNA, DNA, equivalents thereof and/or mixtures comprising one or more of these compounds.

Natural nucleobases include but are not limited to the purines adenine and guanine as well as the pyrimidines cytosine, thymine and uracil.

Natural nucleosides include but are not limited to the ribose nucleosides adenosine, guanosine, uridine and cytidine and the deoxyriboase nucleosides deoxyadenosine, deoxyguanosine, deoxythymidine and deoxycytidine.

Natural nucleotides include but are not limited to phosphate esters of natural nucleosides, such as the monophosphates adenylate (AMP), guanylate (GMP), uridylate (UMP), cytidylate (CMP), deoxythymidylate (dTMP) deoxycytidylate (dCMP), and diphosphates and triphosphates of natural nucleosides such as ADP and ATP.

The amount of nucleobase source to be administered will i.e. depend on the type of treatment desired, e.g. whether prophalactic or therapeutic, and on the subject to be treated, e.g. the eating habits of the individual, whether the subject to be treated is a child or adult and the like. Thus, a heavy meat eater will possibly have greater nucleobase source supply requirements than a person on a vegetable diet. In general, for larger mammals including humans, satisfactory results will be obtained with 1 to 50 times the normal daily amount of ca. 0.5 to 1.5 g RNA corresponding with about 0.1 to 75 g RNA, DNA, nucleosides or nucleotides per day or an equivalent amount in the form of nucleobases.

For the purpose of this invention one weight unit of nucleobase is regarded to be equivalent with 2.5 to 3 weight units of RNA, DNA, nucleosides or nucleotides. For convenience, the following daily amounts are expressed in g RNA only.

For long term or nutritional use, the daily amount of nucleobase source to be administered will conveniently vary within the range of from 0.1 to 4 g RNA, preferably of from 1 to 3 g RNA, in particular of from 1.5 to 2.5 g RNA.

For short term or therapeutical use, the daily amount will in general be higher. For acute treatment with high amounts of nucleobase sources, it is preferred to employ pyrimidine nucleobase sources such as uridine or uracil. Preferred daily amounts for therapeutic use are from 100% to 2000% in excess of normal amounts, corresponding with from about 0.5 g to 30 g RNA. More preferred amounts for therapeutical use are in the range of from 1 g to 20 g RNA, in particular of from 1 g to 7.5 g RNA per day. Pharmaceutical compositions may compromise a daily amount or parts thereof, e.g. in unit doses suitable for three or four applications per day.

The method and compositions of the invention may be employed in any situation where a stimulation of the immune function is desirable, e.g. for restoring a normal immune response, for abating the immunosuppressive effect of an immunosuppressant agent, for enhancing the development of the immune system in a developing mammal, for enchancing the activity of senescent immune system of a mammal and the like.

In the following examples, tables and figures illustrating the invention:

F is standard laboratory chow supplied by Purina under the code number 5008 and comprising 23.5% weight of a protein source from soybean, fish-bone meal and milk.

NF is a nucleotide free diet supplied by Purina under the number 5755, comprising 21% by weight of casein as its protein source and only traces (less than 0.001% by weight according to HPLC analysis) of nucleotides. NF is isocaloric and isonitrogenous with F.

NFR is NF supplemented with RNA (purified yeast RNA).

NFR (0.25%) is NFR supplemented with 0.25% by weight purified yeast RN.

NFA is NF supplemented with adenine.

NFU is NF supplemented with uracil.

PF is NF without protein, supplied by Purina under the code number 5765.

PFR is PF supplemented with RNA (purified yeast RNA)

PFA is PF supplemented with adenine.

PFU is PF supplemented with uracil.

PLN stands for popliteal lymph nodes.

DESCRIPTION OF THE DRAWINGS

FIG. 1 represents the effect of protein free diet on mouse body weight;

FIG. 2 represents the PLN delta values after protein free diet tx.;

FIG. 3 represents the dose response Pf—NFR, NFU—PLN;

FIG. 4 represents the MOLT-4 growth plus or minus nucleosides, and

Examples

Figure 5:
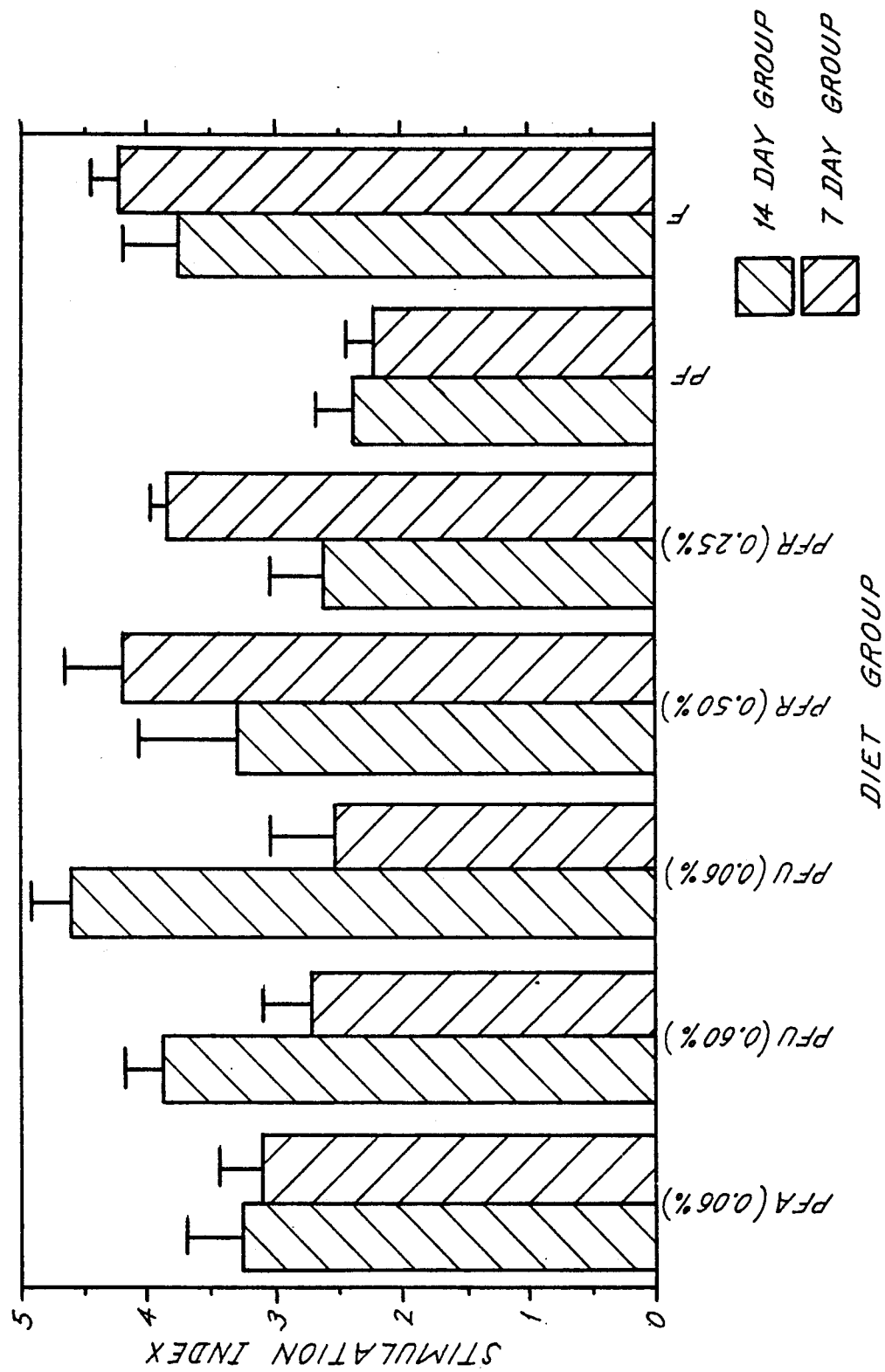
FIG. 5 represents the anlaysis of seven day PLN response after 7 or 14 days on diet.

The stimulation index was calculated as follows:

$$\text{Stimulation index (S.I.)} = \frac{\text{Weight of allogeneically sensitized } PLN \text{ in mg}}{\text{Weight of syngeneically sensitized } PLN \text{ in mg}}$$

EXAMPLE 1

Dietary Nucleotides—Effect on Immunorestoration

Mice were placed on a protein free diet (PF-Purina 5765). The animals were maintained on this diet for either six or eleven days and then switched to chow (F), 5755 (NF) or 5755 supplemented with various levels of RNA (NFR) or uracil (NFU).

Six to eight weeks after the switch of RF to F, NF, or NFR or NFA all animals were used for the following in vivo assay.

The animals were inoculated with irradiated (3000R) $10^7$ $C_{57}Bl/6$ allogenic spleen cells in the right hind footpad, while the left hind footpad received (3000R) $10^7$ Balb/C syngeneic cells spleen as controls.

Seven days after the inoculations, mice were sacrificed and the popliteal lymph nodes (PLN) were excised and weighed. The weights of the mice in the 6 day experiment are shown in FIG. 1 and the PLN delta values plotted in FIG. 2. The actual data is given in Table 1. The F group was maintained on chow (F) throughout the experiment and was never given the protein free diet so they represent a normal control. This study shows that repletion of protein while restoring the body weight was not suffieient to restore any immune response in these mice while RNA addition gave considerable restoration of cellular immune function in a relatively short time period.

The same system was used to detemine dose related effects of nucleotides. Mice were maintained on the protein free diet for 13 days and then converted to 5755 (NF) diet with 0.025% RNA (1/10 normal), 2.5% RNA (10X normal) or 0.6% uracil (10X normal) and the PLN assay started. The results are shown in FIG. 3 with data in Table 2, 4 and 5. In a separate experiment, shown in Table 3, a group of mice on the protein free diet were switched to chow diet and compared to 2.5% RNA and 0.6% uracil groups. The recovery of activity was significantly less in chow than in both high level nucleotide groups. It is clear from these studies that higher levels of uracil or RNA than normally found in the diet were more effective in restoring lost immune function.

EXAMPLE 2

MOLT-4 Human T-Lymphoblast Growth in Serum free RPMI-1640+Human IL-2+Nucleosides in Vitro:

Experiments have shown that the murine IL-2 dependent helper T-cell line (HT-2) requires nucleosides (uridine and inosine) for optimal $G_1$ to S phase transition in serum free media. Uridine alone was particularly effective. To determine nucleoside requirement in human cultured T-cell lines, preliminary growth kinetic experiments using the human T-lymphoblast cell line MOLT-4 were run. This cell line produces IL-2 after stimulation with lectins and phorbol esters. Long-term culture of this cell line is not II-2 dependent but responds to IL-2. MOLT-4 cells were arrested at $G_0/G_1$ phase following extensive washing and removal of Fetal Bovine Serum. Cell cultures were planted at a cell density of $5 \times 10^4$ cells/ml RPMI-1640 with 20 $\mu$M hepes and 2 mM L-glutamine. Human IL-2 (5 $\mu$/ml) and uridine (100 $\mu$M) was added to cell cultures at time 0 and viable cell number was monitored at various time points for 72 hours.

The results (FIG. 4) show that adding uridine (100 $\mu$M) to serum free MOLT-4 cultures in the presence of IL-2 increased $G_1$-S phase transition in terms of viable cell number and over a time course (i.e., $G_1$-S phase transition occurred at 20 hours in cultures with uridine and 40 hours in cultures without uridine). Other experiments show that adenosine+inosine+uridine in combination is more effective than uridine alone.

EXAMPLE 3

Dietary Nucleotides—Prevention of immune function loss with protein or amino acid starvation After several weeks on rat chow mice (10 in each group) were placed on a protein free diet (PF-Purina 5765) or protein free diets with various additions of nucleobase sources; PFR (Purina 5765 with either 0.25% or 0.50% w/w yeast RNA added as indicated), PFU (Purina 5765 with either 0.06% or 0.60% w/w uracil added as indicated) and PFA (Purina 5765 with 0.06% w/w adenine addeed). Normal rat chow F (Purina 5008) was also used as a normal control diet.

In one set of animals on all diets the PLN assay(described in Example 1) was done by injecting the mice on the day the diets were changed and the lymph nodes were harvested after seven days on the indicated diet. In the second set of animals the injections were done on the seventh day and the lymph nodes harvested seven days later, the fourteenth day on the diet.

The results are shown below in Tables 6 and 7 and FIG. 5. It is clear from these studies that addition of a source of nucleobases to the nucleotide-free, protein-free diet PF allowed retention of in vivo cellular immune function as measured by the PLN assay. RNA addition was particularly effective in the seven day experiment while uracil addition was more effective in the 14 day PLN experiment. This maintenance of immune function was not expected in the light of previous work that suggests that sources of amino acids are one of the most critical components in maintenance of immune function.

TABLE 1

Protein Free Diet Induced Immunosuppression And Its Reversibility With Dietary Nucleotides.

| Diet | Allogeneic lymphnode (mgs) | Syngeneic lymphnode (mgs) | Delta[1] | Stim.[2] Index |
|---|---|---|---|---|
| F | 10.7 | 3.1 | 7.6 | 3.45 |
|  | 9.3 | 4.0 | 5.3 | 2.33 |
|  | 8.4 | 2.0 | 6.4 | 4.20 |
|  | 6.2 | 2.3 | 3.9 | 2.69 |
|  | 6.5 | 1.4 | 5.1 | 4.64 |
| X ± SEM | 8.2 ± 0.9 | 2.6 ± 0.6 | 5.7 ± 0.6 | 3.5 ± 0.4 |
| PF to NF | 1.6 | 1.9 | −0.3 | 0.84 |
|  | 1.7 | 1.7 | 0.0 | 1.00 |
|  | 1.6 | 2.0 | −0.4 | 0.80 |
|  | 1.2 | 2.2 | −1.0 | 0.55 |
|  | 2.5 | 1.2 | 1.3 | 2.08 |
| X ± SEM | 1.7 ± 0.2 | 1.8 ± 0.2 | −0.8 ± 0.4 | 1.1 ± 0.3 |
| PF to NFR | 4.3 | 0.8 | 3.5 | 5.38 |
|  | 3.7 | 1.8 | 1.9 | 2.05 |
|  | 3.1 | 0.6 | 2.5 | 5.16 |
|  | 4.6 | 1.2 | 3.4 | 3.83 |
|  | 2.8 | 0.4 | 2.4 | 7.00 |
| X ± SEM | 3.7 ± 0.3 | 1.0 ± 0.3 | 2.8 ± 0.3 | 4.7 ± 0.8 |
| PF alone | 0.66 | 0.90 | −0.24 | 0.73 |
|  | 0.72 | 0.92 | −0.20 | 0.78 |
|  | 0.94 | 0.75 | 0.19 | 1.25 |
|  | 0.85 | 1.00 | −0.15 | 0.85 |
|  | 1.45 | 1.10 | 0.35 | 1.32 |
| X ± SEM | 0.9 ± 0.1 | 0.9 ± 0.06 | −0.01 ± 0.1[a] | 1.0 ± 0.1 |

[1]Delta = allo lymphnode minus syn lymphnode
[2]Stim. Index = S.I. = allo lymphnode divided by syn lymphnode weight
[a]PF vs F, PF to NFR $p < 0.002$ vs PF, NF $p < 0.85$

TABLE 2

Body weights (gms) of Day 18 PLN experiment

| Diet group | Day 1 | Day 11 | Day 18 |
|---|---|---|---|
| PF | 23.5 ± 0.7 | 18.2 ± 1.3 | 16.6 ± 0.9 |
| PF-NFR (0.025%) | 22.8 ± 1.7 | 18.3 ± 1.0 | 23.1 ± 1.5 |
| PF-NFR (2.5%) | 23.0 ± 2.5 | 18.5 ± 2.1 | 23.5 ± 2.7 |
| PF-NFU (0.6%) | 22.6 ± 1.9 | 17.3 ± 1.3 | 24.4 ± 1.9 |
| F | 22.0 ± 0.8 | 22.7 ± 0.9 | 23.0 ± 0.9 |

Day 1 - mice started on PF diet.
Day 11 - diet switch and PLN assay set up.
Day 18 - PLN harvest and results.

TABLE 3

Dietary Nucleotide Dose Response Following PF Induced Immunosuppression.

| Diet group | Allo LNs (mgs) | Syn LNs (mgs) | Delta (allo-syn) | Stim. Index (allo/syn) |
|---|---|---|---|---|
| PF | 3.3 | 0.7 | 2.6 | 4.7 |
|  | 4.2 | 1.0 | 3.2 | 4.2 |
|  | 2.9 | 2.0 | 0.9 | 1.4 |
|  | 4.0 | 1.3 | 2.7 | 3.1 |
|  | 0.9 | 0.9 | 0.0 | 1.0 |
|  | 3.1 ± 0.6 | 1.2 ± 0.2 | 1.2 ± 0.6 | 2.9 ± 0.7 |
| PF–NFR (0.025%) | 6.5 | 1.3 | 5.2 | 5.0 |
|  | 8.6 | 1.8 | 6.8 | 4.8 |
|  | 8.7 | 2.0 | 6.7 | 4.3 |
|  | 7.7 | 2.1 | 5.6 | 3.7 |
|  | 5.6 | 1.5 | 4.1 | 3.7 |
|  | 7.4 ± 0.6 | 1.7 ± 0.2 | 5.7 ± 0.5 | 4.3 ± 0.3 |
| PF–NFR (2.5%) | 9.7 | 1.5 | 8.2 | 6.5 |
|  | 5.9 | 1.3 | 4.6 | 4.5 |
|  | 4.7 | 1.9 | 2.8 | 2.5 |
|  | 7.2 | 1.0 | 6.2 | 7.2 |
|  | 7.4 | 1.2 | 6.2 | 6.2 |
|  | 7.0 ± 0.8 | 1.4 ± 0.2 | 5.6 ± 0.9 | 5.4 ± 0.8 |
| PF–NFU (0.6%) | 10.3 | 1.5 | 8.8 | 6.7 |
|  | 9.2 | 1.5 | 6.7 | 6.1 |
|  | 9.5 | 1.6 | 7.9 | 5.9 |
|  | 13.0 | 2.1 | 11.1 | 6.2 |
|  | 6.8 | 1.6 | 5.2 | 4.2 |
|  | 9.8 ± 1.0 | 1.7 ± 0.3 | 7.9 ± 1.0 | 5.8 ± 1.0 |
| F–F | 6.0 | 1.8 | 4.2 | 3.3 |
|  | 11.6 | 1.4 | 10.2 | 8.3 |
|  | 8.3 | 2.2 | 6.1 | 3.8 |
|  | 6.2 | 0.7 | 5.5 | 8.9 |
|  | 10.9 | 1.2 | 9.7 | 9.1 |
|  | 8.6 ± 1.2 | 1.5 ± 0.3 | 7.1 ± 1.2 | 6.7 ± 1.3 |

AlloLNs: $C_{57}81/6$ lymphnodes,
SynLNs: Balb/c lymphnodes.
PF started day one, dosaged diets and PLN assay day 11 harvested day 18

| PF vs PF–NFR0.025% | $p < 0.01$ | N.S. |
|---|---|---|
| vs PF–NFR2.5% | $< 0.01$ | $< 0.05$ |
| vs PF–NFU0.6% | $< 0.001$ | $< 0.05$ |
| vs F | $< 0.01$ | $< 0.05$ |

TABLE 4

Dietary Nucleotide Dose Response Following PF Induced Immunosuppression.

| Diet Group | Allo LNs (mgs) | Syn LNs (mgs) | Delta (allo-syn) | Stim. Index (allo/syn) | p |
|---|---|---|---|---|---|
| PF | 1.8 | 0.5 | 1.3 | 3.6 |  |
|  | 1.6 | 0.8 | 0.8 | 2.0 |  |
|  | 1.0 | 0.6 | 0.4 | 1.7 |  |
|  | 1.6 | 1.9 | −0.3 | 0.8 |  |
|  | 2.2 | 1.2 | 1.0 | 1.8 |  |
| Avg ± SEM | 1.6 ± 0.2 | 1.0 ± 0.3 | 0.6 ± 0.3 | 2.0 ± 0.5 | >0.1 |
| PF–F | 3.1 | 1.5 | 1.6 | 2.1 |  |
|  | 3.6 | 1.4 | 2.2 | 2.6 |  |
|  | 5.4 | 2.0 | 3.4 | 2.7 |  |
|  | 4.7 | 1.1 | 3.6 | 4.3 |  |
|  | 10.4 | 3.6 | 6.8 | 2.9 |  |
|  | 5.4 ± 1.3 | 1.9 ± 0.4 | 3.5 ± 0.9 | 2.9 ± 0.4 | >0.2 |
| PF–NF | 2.3 | 1.6 | 0.7 | 1.4 |  |
|  | 4.1 | 2.0 | 2.1 | 2.1 |  |
|  | 6.1 | 2.5 | 3.6 | 2.4 |  |
|  | 3.7 | 2.8 | 0.9 | 1.3 |  |
|  | 3.6 | 1.4 | 2.2 | 2.6 |  |
|  | 4.0 ± 0.6 | 2.1 ± 0.3 | 1.9 ± 0.5 | 2.0 ± 0.6 |  |
| PF–NFR (0.025%) | 4.2 | 1.5 | 2.7 | 2.8 |  |
|  | 3.8 | 2.5 | 1.3 | 1.5 |  |
|  | 3.5 | 1.5 | 2.0 | 2.3 |  |
|  | 3.4 | 1.4 | 2.0 | 2.4 |  |
|  | 4.2 | 1.8 | 2.4 | 2.3 |  |
|  | 3.8 ± 0.8 | 1.7 ± 0.2 | 2.1 ± 0.2 | 2.3 ± 0.2 | >0.8 |
| PF–NFR (0.25%) | 5.1 | 2.8 | 2.3 | 1.8 |  |
|  | 3.9 | 1.5 | 2.4 | 2.6 |  |
|  | 3.9 | 1.7 | 2.2 | 2.3 |  |
|  | 5.6 | 1.8 | 3.8 | 3.1 |  |
|  | 6.4 | 1.3 | 5.1 | 4.9 |  |
|  | 5.0 ± 0.5 | 2.0 ± 0.3 | 3.2 ± 0.6 | 2.9 ± 0.5 | >0.2 |
| PF–NFR (2.5%) | 7.0 | 2.7 | 4.3 | 2.6 |  |
|  | 8.7 | 3.6 | 5.1 | 2.4 |  |

TABLE 4-continued

Dietary Nucelotide Dose Response Following PF Induced Immunosuppression.

| Diet Group | Allo LNs (mgs) | Syn LNs (mgs) | Delta (allo-syn) | Stim. Index (allo/syn) | p |
|---|---|---|---|---|---|
| | 8.5 | 3.1 | 5.4 | 2.7 | |
| | 6.2 | 3.0 | 3.2 | 2.1 | |
| | 7.4 | 2.8 | 4.6 | 2.6 | |
| | 7.6 ± 0.5 | 3.0 ± 0.2 | 4.5 ± 0.4 | 2.5 ± 0.1 | >0.01 |
| PF-NFU | 4.6 | 2.4 | 2.2 | 1.9 | |
| (0.06%) | 4.4 | 1.6 | 2.8 | 2.8 | |
| | 5.5 | 0.9 | 4.6 | 6.1 | |
| | 9.2 | 2.1 | 7.1 | 4.4 | |
| | 8.2 | 2.6 | 5.6 | 3.2 | |
| | 6.4 ± 1.0 | 1.9 ± 0.3 | 4.9 ± 0.9 | 3.7 ± 0.7 | >0.01 |
| PF-NFU | 4.2 | 0.5 | 3.7 | 8.4 | |
| (0.6%) | 4.9 | 1.3 | 3.6 | 3.8 | |
| | 5.5 | 1.4 | 4.1 | 3.9 | |
| | 6.2 | 1.5 | 4.7 | 4.1 | |
| | 6.3 | 1.6 | 4.7 | 3.9 | |
| | 5.4 ± 0.4 | 1.3 ± 0.2 | 4.2 ± 0.2 | 4.8 ± 0.9 | >0.01 |
| F--F | 8.3 | 1.7 | 6.6 | 4.9 | |
| | 8.8 | 2.2 | 6.6 | 4.0 | |
| | 8.7 | 2.7 | 6.0 | 3.2 | |
| | 6.8 | 1.9 | 4.9 | 3.6 | |
| | 6.4 | 2.1 | 4.3 | 3.0 | |
| | 7.8 ± 0.5 | 2.1 ± 0.2 | 5.7 ± 0.5 | 3.7 ± 0.8 | >0.001 |

AlloLNs: $C_{57}Bl/6$ lymphnodes
SynLNs: Balb/c lymphnodes
PF started on day 1, dosaged diets and PLN assay day 9, LNs harvested on day 16
p values = PF-NF vs individual groups (calculated by student T test)

TABLE 5

Body Weights (gms) of Day 16 PLN Experiment

| Diet group | Day 8 | Day 12 | Day 16 |
|---|---|---|---|
| PF | 15.2 ± 0.9 | 17.2 ± 0.6 | 13.7 ± 0.6 |
| NFU (0.6%) | 19.7 ± 0.7 | 22.0 ± 0.9 | 21.7 ± 0.7 |
| NFU (0.06%) | 18.8 ± 0.5 | 22.3 ± 0.6 | 19.4 ± 1.1 |
| NFR (2.5%) | 18.6 ± 0.9 | 21.7 ± 0.4 | 22.5 ± 0.5 |
| NFR (0.25%) | 18.7 ± 0.3 | 21.6 ± 0.5 | 20.2 ± 0.6 |
| NFR (0.025%) | 17.2 ± 0.6 | 20.5 ± 0.6 | 19.8 ± 0.6 |
| NF | 19.7 ± 0.8 | 23.3 ± 0.9 | 22.5 ± 0.8 |
| PF--F | 18.5 ± 0.3 | 23.2 ± 0.4 | 22.1 ± 0.4 |
| F | 23.6 ± 0.7 | 23.3 ± 0.4 | 21.5 ± 0.6 |

TABLE 6

Effect of PF and various PF supplemented diets on the immune response as measured by PLN assay, 7 days following diet change.

| Diet | Syn (mgs) | Allo (mgs) | Delta* | S.I.** |
|---|---|---|---|---|
| F | 1.14 ± .03 | 4.83 ± .51 | 3.69 ± .51 | 4.24 ± .46 |
| PF | 1.18 ± .04 | 2.65 ± .42 | 1.47 ± .39 | 2.23 ± .30 |
| PFR 0.25% | 1.06 ± .10 | 4.11 ± .73 | 3.05 ± .65 | 3.85 ± .42 |
| PFR 0.50% | 0.75 ± .07 | 3.13 ± .58 | 2.38 ± .56 | 4.20 ± .78 |
| PFU 0.06% | 1.17 ± .05 | 2.94 ± .30 | 1.77 ± .33 | 2.55 ± .31 |
| PFU 0.60% | 0.98 ± .10 | 2.63 ± .31 | 1.66 ± .25 | 2.72 ± .30 |
| PFA 0.06% | 1.05 ± .09 | 3.12 ± .24 | 2.08 ± .31 | 3.09 ± .44 |

TABLE 7

Effect of PF and various PF supplemented diets on the immune response as measured by PLN assay, 14 days following diet change.

| Diet | Syn (mgs) | Allo (mgs) | Delta* | S.I.** |
|---|---|---|---|---|
| F | 1.47 ± .10 | 5.41 ± .76 | 3.93 ± .10 | 3.75 ± .21 |
| PF | 0.84 ± .07 | 1.96 ± .14 | 1.12 ± .13 | 2.38 ± .21 |
| PFR 0.25% | 0.83 ± .05 | 2.14 ± .08 | 1.31 ± .07 | 2.63 ± .13 |
| PFR 0.5% | 0.60 ± .05 | 1.84 ± .17 | 1.25 ± .19 | 3.30 ± .47 |
| PFU 0.06% | 0.48 ± .05 | 2.04 ± .13 | 1.56 ± .11 | 4.63 ± .49 |
| PFU 0.6% | 0.55 ± .04 | 2.08 ± .19 | 1.53 ± .18 | 3.89 ± .37 |
| PFA 0.06% | 0.51 ± .05 | 1.63 ± .19 | 1.11 ± .17 | 3.26 ± .36 |

*Delta = Wt. of Allogeneic lymph node-Wt. of Syngenic lymph node
**S.I. = $\frac{\text{Wt. of Allogeneic lymph node}}{\text{Wt. of Syngeneic lymph node}}$
Day 0 Start on various Diets
Day 7 PLN assay performed.
Day 14 Harvest PLNs.

What is claimed is:

1. A method of stimulating the immune function in a mammal, which comprises administering to a subject in need of such treatment due to malnutrition or protein starvation a substantially protein-free dietary or pharmaceutical composition comprising an immunostimulatory amount of a nucleobase source and a pharmaceutically or nutritionally acceptable excipient or carrier, said immunostimulatory amount of said nucleobase source comprising about 0.1 to about 75 grams per day of RNA.

2. A pharmaceutical or dietary composition for administering to a mammal with malnutrition or protein starvation, said composition being substantially protein-free and comprising an immunostimulatory amount of a nucleobase source and a pharmaceutically or nutritionally acceptable excipient or carrier, wherein said immunostimulatory amount of said nucleobase source comprises about 0.1 to about 75 grams of RNA administered per day.

3. The pharmaceutical composition of claim 2, comprising conventional, pharmaceutically acceptable excipients in enteral or parenteral application form.

4. The composition of claim 2, comprising one or more of the components selected from vitamins, minerals and trace elements.

5. The composition of claim 2 comprising an administration unit per day, whereby, said administration unit is divided into shaped sub-units, where more than one administration per day is indicated.

6. A dietary composition of claim 5, comprising from 0.1 to 4.0 g RNA per administration unit for a day.

7. A dietary composition of claim 5, comprising from 1 to 3 g, RNA per administration unit for a day.

8. A pharmaceutical composition of claim 5, comprising from 0.5 to 30 g RNA per administration unit for a day.

9. A method for the maintenance of the immune function in a mammal with protein depletion or starvation comprising administering to said human or animal the composition of claim 2.

* * * * *

UNITED STATES PATENT AND TRADEMARK OFFICE
CERTIFICATE OF CORRECTION

| | |
|---|---|
| PATENT NO. | : 5,268,365 |
| APPLICATION NO. | : 07/767302 |
| DATED | : December 7, 1993 |
| INVENTOR(S) | : Frederick B. Rudolph and Charles T. Van Buren |

It is certified that error appears in the above-identified patent and that said Letters Patent is hereby corrected as shown below:

In column 1, line 13, insert --This invention was made with government support under grant numbers CA014030 and CA035492 awarded by the National Institutes of Health. The government has certain rights in the invention.--.

Signed and Sealed this

Seventh Day of April, 2009

JOHN DOLL
*Acting Director of the United States Patent and Trademark Office*